United States Patent
Fukuhira et al.

(10) Patent No.: US 8,097,273 B2
(45) Date of Patent: *Jan. 17, 2012

(54) BIODEGRADABLE FILM HAVING HONEYCOMB STRUCTURE

(75) Inventors: Yukako Fukuhira, Tokyo (JP); Eiichi Kitazono, Tokyo (JP); Hiroaki Kaneko, Tokyo (JP); Yoshihiko Sumi, Tokyo (JP); Masatsugu Shimomura, Hokkaido (JP); Masaru Tanaka, Hokkaido (JP)

(73) Assignee: Teijin Limited, Osaka (JP)

( * ) Notice: Subject to any disclaimer, the term of this patent is extended or adjusted under 35 U.S.C. 154(b) by 836 days.

This patent is subject to a terminal disclaimer.

(21) Appl. No.: 10/552,685

(22) PCT Filed: Apr. 8, 2004

(86) PCT No.: PCT/JP2004/005068
§ 371 (c)(1),
(2), (4) Date: Oct. 11, 2005

(87) PCT Pub. No.: WO2004/089434
PCT Pub. Date: Oct. 21, 2004

(65) Prior Publication Data
US 2006/0189911 A1   Aug. 24, 2006

(30) Foreign Application Priority Data

Apr. 10, 2003  (JP) .................... 2003-106186
Aug. 7, 2003   (JP) .................... 2003-288573

(51) Int. Cl.
*A61F 13/00* (2006.01)
*A61F 2/00* (2006.01)
(52) U.S. Cl. ...................... 424/443; 424/426
(58) Field of Classification Search ................ None
See application file for complete search history.

(56) References Cited

U.S. PATENT DOCUMENTS 5,283,122 A * 2/1994 Huang et al. ............. 428/402.2
2003/0044455 A1* 3/2003 Kazakov et al. ............ 424/450

FOREIGN PATENT DOCUMENTS

| JP | 60-014861 A | 1/1985 |
| JP | 11-192299 A | 7/1999 |
| JP | 2000-197693 A | 7/2000 |
| JP | 2001-157574 A | 6/2001 |
| JP | 2002-335949 A | 11/2002 |
| JP | 2002-347107 A | 12/2002 |
| WO | 98/02171 A1 | 1/1998 |
| WO | 01/46265 A1 | 6/2001 |

OTHER PUBLICATIONS

Johnsson et al. Biophysical Journal 2001 80:313-323.*
Nishikawa et al. Materials Research Society Symposium Proceedings 2002 724:N11.7.1-N11.7.6.*
Maruyama et al. Thin Solid Films 1998 327-329:854-856.*
Zhao et al. Journal of Applied Polymer Science 2003 90:1846-1850.*
Berge et al. Physical Review A 1990 41:6893-6902.*
Takehiro Nishikawa, Jin Nishida, Ryusuke Ookura, Shin-Ichiro Nishimura, Shigeo Wada, Takeshi Karino, and Masatsugu Shimomura; Mesoscopic patterning of cell adhesive substrates as novel biofunctional interfaces; Materials Science and Engineering C 10 (1999) 141-146.
Olaf Karthaus, Norihiko Maruyama, Xavier Cieren, Masatsugu Shimomura, Hirokazu Hasegawa, and Takeji Hashimoto; Water-Assisted Formation of Micrometer-Size Honeycomb Patterns of Polymers; Langmuir the ACS Journal of Surfaces and Colloids; Jul. 25, 2000, vol. 16, No. 15; pp. 6071-6076.
Takehiro Nishikawa, Jin Nishida, Ryusuke Ookura, Shin-Ichiro Nishimura, Shigeo Wada, Takeshi Karino, Masatsugu Shimomura; Honeycomb-patterned thin films of amphiphilic polymers as cell culture substrates; Materials Science and Engineering C 8-9 (1999) 495-500.
Takehiro Nishikawa et al., Fabrication of Honeycomb Film of an Amphiphilic Copolymer at the Air-Water Interface, Langmuir, vol. 18, No. 15, pp. 5734 to 5740, 2002, Fig. 1.
Ryusuke Ookura et al., Stabilization of Micro patterned Polymer Film as Artificial Extra cellular Matrices for Tissue Engineering, Mol. Cryst. and Liq. Cryst., vol. 337, pp. 461 to 464, 1999, Abstract.
Takehiro Nishikawa et al., Fabrication of Honeycomb Film of an Amphiphilic Copolymer at the Air-Water Interface, Langmuir, vol. 18, No. 15, pp. 5734 to 5740, 2002, Fig. 1.
Ryusuke Ookura et al., Stabilization of Micro patterned Polymer Film as Artificial Extra cellular Matrices for Tissue Engineering, Mol. Cryst. and Liq. Cryst., vol. 337, pp. 461 to 464, 1999, Abstract.
Yamaoka, T. et al., 20) Decomposition Characteristics of Novel Biodegradable Polylactic Acid-Polyether Copolymer and in Vivo Evaluation as Antiadhesive Film, The Society of Polymer Science, 27th Medical Macromolecule Symposium, 1998, pp. 43-44, Japan.
Yamaoka, T. et al., 3H05 Novel Antiadhesive Film Using Biodegradable Block Polymer, The Society of Fiber Science and Technology, Sen-I Gakkai Symposia Preprints, 1998, Japan.
Onoriaki, K. et al., 1-Pc-1 A Prospective Study for So-Called "Congenital" Trigger Thumb Based on the Medical Check for 1,130 Newborn Infants, 2003, p. S95, vol. 20, No. 1, Japan.
Ookura et al; Stabilizarion of Micropatterned Polymer Films as Artificial Extracellular Matrices for Tissue Engineering; Mol. Cryst. and Liq. Cryst., vol. 337, pp. 461-464 (1999).
Nishikawa et al; Honeycomb-patterned thin films of amphiphilic polymers as cell culture substrates; Materials Science & Engineering; C 8-9 (1999) pp. 495-500.

* cited by examiner

*Primary Examiner* — Juliet Switzer
*Assistant Examiner* — Caralynne Helm
(74) *Attorney, Agent, or Firm* — Sughrue Mion, PLLC

(57) ABSTRACT

The invention relates to a honeycomb film made of a biodegradable polymer which has biodegradation properties as an anti-adhesion membrane for preventing adhesion after an operation, is excellent in handling properties, and exhibits a satisfactory adhesion preventive effect stably over a desired period of time, and to a production process of the same. Above all, the invention provides an anti-adhesion membrane of a honeycomb film made of polylactic acid as a biodegradable polymer and a phospholipid and a production process of the same.

12 Claims, 2 Drawing Sheets

10 μm

BIODEGRADABLE FILM HAVING HONEYCOMB STRUCTURE

TECHNICAL FIELD

The present invention relates to an anti-adhesion membrane for preventing adhesion after an operation. In more detail, the invention relates to an anti-adhesion membrane made of a biodegradable film having a honeycomb structure. The anti-adhesion membrane of the invention is excellent in handling properties and exhibits a satisfactory adhesion preventive effect stably over a desired period of time.

BACKGROUND ART

Tissue adhesion which is a physiological action as generated after a surgical operation is defined as abnormal binding between a surrounding tissue and an organ or the like, which is caused from the production of a collagen fiber by a fibroblast as generated following a tissue damage. It is considered that such adhesion occurs at a probability of 90% after the operation, and in the case where a pain, a biofunctional disorder, or the like is caused, a patient is accompanied by mental or physical pain, resulting in a problem.

In order to solve this problem, there have hitherto been made a number of studies. For example, in order to minimize the adhesion formation, water-soluble anti-adhesion membrane such as a sodium alginate aqueous solution and a sodium hyaluronate aqueous solution were used. However, while these materials have some anti adhesive effect, because of their water solubility, they also flow out of the site where prevention of adhesion is required, they do not retain in a necessary place, and they have a possibility to cause undesired adhesion in a normal area.

For that reason, in order to separate a damaged tissue from other tissues, anti-adhesion membrane made of, as a physical barrier, a material such as silicone, vaseline, and polytetrafluoroethylene are studied. Since such a material is a non-bioabsorbable material, while it is provided with a sufficient action as a barrier, there were involved problems such as a risk of an immune response due to long-term retention in the body and a necessity of a second operation for taking out it after cure.

In order to solve these problems, anti-adhesion membrane using a natural polymer which is a bioabsorbable material were developed.

Specifically, an anti-adhesion membrane using oxidized cellulose is known. In the case of applying a sponge or knit made of oxidized cellulose, since fibrous cells are liable to pass through voids and migrate, there was involved a problem of causing adhesion. In order to prevent this, anti-adhesion membrane made of sodium hyaluronate and carboxymethyl cellulose are developed and used. However, since these materials have high water absorption, there is involved a problem such that they are swelled by liquid of surgical instruments or organs other than a wound area so that handling properties are poor.

An anti-adhesion membrane is desired to have a shape in which circulation of fibrous cells from one tissue to other tissue does not occur and is also desired to have biodegradability and high operability.

JP-A-2000-197693 discloses a porous anti-adhesion membrane made of a copolymer of lactic acid and caprolactone.

JP-A-2001-157574 describes a film having a honeycomb structure as prepared from a polymer containing a biodegradable polymer having added thereto 1 to 50% of an amphiphilic polymer having a hydrophilic acrylamide polymer as a principal chain skeleton and having both a dodecyl group as a hydrophobic side chain and a lactose group or a carboxyl group as a hydrophilic side chain and a production process thereof.

However, though the base material polymer as used herein is a polymer having high biocompatibility, there is concern that the amphiphilic polymer might be decomposed into acrylamide derivatives, and it is hard to say that the derivatives are always safety against a living body. If possible, it is desired that the amount of use of such an amphiphilic polymer is controlled at a low level as far as possible.

In this way, for the purpose of applying to a biotissue, in the case of using a film having a fine structure, biocompatibility becomes a big problem. For that reason, not only a polymer to be used but also a reagent for forming a fine structure, namely a surfactant such as amphiphilic polymers, is desired to have biocompatibility and safety against a living body. For the purpose of achieving this, it is also desired from the viewpoint of securing safety to increase the content of the polymer and to control the amount of use of the surfactant.

In the existing circumstances, any anti-adhesion membrane which has adequate biodegradability and biocompatibility, is excellent in handling properties and exhibits a satisfactory adhesion preventive effect stably over a desired period of time does not exist, and its appearance is being demanded.

DISCLOSURE OF THE INVENTION

The present inventors have found that a biodegradable film having a honeycomb structure is an anti-adhesion membrane having excellent handling properties and exhibiting a satisfactory adhesion preventive effect stably over a desired period of time.

Also, they have found that by blending a phospholipid with a biodegradable polymer as a surfactant and casting the blend under a high humidity, a film having a honeycomb structure which is also useful as a base material of cell culture and excellent in biocompatibility is obtained and that the subject film is effective for prevention of adhesion of an operation site, etc., leading to accomplishment of the invention.

Specifically, the invention relates to an adhesion preventing material comprising a biodegradable film having a honeycomb structure and to an anti-adhesion membrane comprising a biodegradable film having a mean void inner diameter of the honeycomb structure of not more than 20 μm.

Furthermore, as a production process of the subject anti-adhesion membrane, the invention relates to a production process of an anti-adhesion membrane using a biodegradable polymer film having a honeycomb structure as obtained by casting an organic solvent solution of a biodegradable polymer on a substrate in the atmosphere of a relative humidity of from 50 to 95%, gradually evaporating the subject organic solvent and simultaneously condensing it on the surface of the subject cast liquid, and evaporating fine water droplets as generated by the subject condensation.

In a preferred embodiment of the invention, the biodegradable film having a honeycomb structure is attached as a physical barrier between an operation site and its adjacent tissue to control attachment of the tissue, thereby reducing the formation of adhesion after the operation.

As the biodegradable polymer which is used for the preparation of the biodegradable film in the invention, biodegradable aliphatic polyesters such as polylactic acid, a lactic acid-glycolic acid copolymer, polyhydroxybutyric acid, polycaprolactone, polyethylene adipate, and polybutylene adipate, aliphatic polycarbonates such as polybutylene carbonate and polyethylene carbonate, and the like are preferable from the viewpoint of solubility in an organic solvent. Above all, polylactic acid, a lactic acid-glycolic acid copylmer, and polycaprolactone are desirable from the viewpoints of easy availability, costs, and the like.

In order to simply prepare a honeycomb structure with good reproducibility, it is preferred to use an amphiphilic polymer in addition to the foregoing biodegradable polymer. Taking into consideration the application as an anti-adhesion membrane, it is preferable that the amphiphilic polymer is non-toxic. As the amphiphilic polymer, a polyethylene glycol/polypropylene glycol block copolymer, an amphiphilic polymer having an acrylamide polymer as a principal chain skeleton and having both a dodecyl group as a hydrophobic side chain and a lactose group or a carboxyl group as a hydrophilic side chain, an amphiphilic polymer having, as a hydrophilic group, an ion complex between an anionic high molecular material such as heparin, dextran sulfate, and a nucleic acid including DNA and RNA and a long-chain alkylammonium salt, or a water-soluble protein such as gelatin, collagen, and albumin can be applied.

Furthermore, a biodegradable and amphiphilic polymer may be used. Examples of such a polymer include a polylactic acid-polyethylene glycol block copolymer, a poly-ε-caprolactone-polyethylene glycol block copolymer, and a polymalic acid-polymalic acid alkyl ester block copolymer.

Moreover, in order to simply prepare a honeycomb structure with good reproducibility, a phospholipid may be added as a surfactant in addition to the foregoing biodegradable polymer.

The phospholipid is a substance constituting the biomembrane system and originally exists in a living body. Accordingly, the phospholipid is a substance which has high biocompatibility and which is also applicable in a drug delivery system, and it is known that the phospholipid has high safety. In addition, the phospholipid which is used as a surfactant in the invention is easily available.

With respect to the origin of the phospholipid to be used in the invention, it does not matter whether it is an extract from an animal tissue or an artificially synthesized product. It is desired to apply, as the phospholipid, a member selected from the group consisting of phosphatidyl ethanolamine, phosphatidyl choline, phosphatidyl serine, phosphatidyl glycerol, and derivatives thereof. Phosphatidyl ethanolamine is preferable, and L-α-phosphatidyl ethanolamine dioleoyl is more preferable.

In preparing a honeycomb structure of the invention, since it is essential to form fine water droplet particles on the polymer solution, an organic solvent to be used must be water-insoluble. Examples thereof include halogen based organic solvents such as chloroform and methylene chloride; aromatic hydrocarbons such as benzene, toluene, and xylene; esters such as ethyl acetate and butyl acetate; water-insoluble ketones such as methyl isobutyl ketone; and carbon disulfide. These organic solvents may be used singly or may be used as a mixed solvent which is a combination of these solvents.

The polymer concentration of the total of the biodegradable polymer and the amphiphilic polymer which are dissolved in such an organic solvent is preferably from 0.01 to 10 wt %, and more preferably from 0.05 to 5 wt %. When the polymer concentration is lower than 0.01 wt %, the mechanical strength of the resulting film is insufficient, and therefore, such is not desirable. Also, when it is 10 wt % or more, the polymer concentration is too high so that a sufficient honeycomb structure is not obtained. Furthermore, the composition ratio of the biodegradable polymer to the amphiphilic polymer is from 99/1 to 50/50 (wt/wt). When the amphiphilic polymer composition is not more than 1, a uniform honeycomb structure is not obtained, while when the subject composition is 50 or more, the resulting honeycomb structure fails in stability, especially dynamic stability, and therefore, such is not preferable.

Similarly, the concentration in the solution of the total of the biodegradable polymer and the phospholipid which are dissolved in the foregoing solvent is preferably from 0.01 to 10 wt %, and more preferably from 0.05 to 5 wt %. When the polymer concentration is lower than 0.01 wt %, the dynamic strength of the resulting film is insufficient, and therefore, such is not desirable. Also, when it is 10 wt % or more, the concentration in the solution is too high so that a sufficient honeycomb structure is not obtained. Furthermore, the composition ratio of the biodegradable polymer to the phospholipid is from 1/1 to 1,000/1 (wt/wt) in terms of a weight ratio. When the weight ratio of the phospholipid to the biodegradable polymer is not more than 1/1,000, a uniform honeycomb structure is not obtained, while when the subject weight ratio is 1/1 or more, the resulting structure does not have self-supporting properties as a film and is high in costs and poor in economy, and therefore, such is not preferable.

In the invention, the subject polymer organic solvent solution is cast on a substrate to prepare a honeycomb structure. As the subject substrate, inorganic materials such as glass, a metal, and a silicon wafer; high molecular materials having excellent organic solvent resistance, such as polypropylene, polyethylene, and polyether ketone; and liquids such as water, a liquid paraffin, and a liquid polyether can be used. Above all, in the case of using water as the substrate, by efficiently utilizing self-supporting properties which are a characteristic feature of the subject honeycomb structure, the subject structure can be easily taken out singly from the substrate, and such is suitable.

In the invention, the mechanism for forming a honeycomb structure is considered as follows. When the hydrophobic organic solvent is evaporated, it takes away a latent heat. Thus, the temperature of the cast film surface drops, and fine liquid droplets of water coagulate and adhere on the surface of the polymer solution. By the action of the hydrophilic segment in the polymer solution, a surface tension between water and the hydrophobic organic solvent is reduced. For that reason, when the water fine particles coagulate to form a single block, they are made stable. Following the evaporation of the solvent, liquid droplets in a hexagonal form lie in the closest packing form, and the water is finally evaporated off, whereby the polymer remains in the regularly laid honeycomb form. Accordingly, with respect to the circumstance for preparing the subject film, it is desired that the relative humidity is in the range of from 50 to 95%. When the relative humidity is not more than 50%, condensation on the cast film is insufficient, while when it is 95% or more, it is difficult to control the circumstance, and therefore, such is not preferable. The size of a void inner diameter of the thus formed honeycomb structure is from 0.1 to 20 μm, and when the size of the void inner diameter falls within this range, the resulting film can be suitably used as an anti-adhesion membrane.

In the thus prepared film, when the surface has a honeycomb structure and the film thickness is sufficiently thick, the back side which comes into contact with the substrate is a flat surface into which pores do not penetrate. Also, when the film thickness is thinner than the size of the water droplet, a film into which pores penetrate is obtained.

Accordingly, it is desired to choose a penetrating film or a non-penetrating film depending upon the intended purpose of use.

From the viewpoint of prevention of adhesion, in order to suppress migration of fibrious cells between the organs, it is preferred to use a film into which pores do not penetrate. Furthermore, it is preferable that the side having a honeycomb structure is brought into contact with a wound area. This is because it is possible to absorb blood or an organ liquid as generated in the wound area into the honeycomb structure and to prevent its exudation into the outside.

The anti-adhesion membrane of the invention can be formed into a shape of a laminate of two or more sheets of honeycomb structure films in consideration of improvement in the mechanical strength. The number of sheets of honeycomb structure films to be laminated is preferably from 2 to 15, and more preferably from 2 to 10 from the viewpoint of flexibility of the film. In this way, it is possible to bring characteristics which polymers constituting the respective films have, such as dynamic strength, tissue adhesion, and bioabsorbability, to the anti-adhesion membrane.

The adhesion preventing material comprising a laminate of honeycomb structure films can be produced by swelling honeycomb structure films to be laminated them, or laminating respective honeycomb structure films and swelling them in an adequate solvent, followed by drying. As the solvent for swelling the dried films, any solvent can be used so far as it swells the honeycomb structure films without dissolving them therein. For example, water or an aqueous solution of an inorganic salt such as sodium chloride and calcium chloride is preferable. Also, an organic solvent such as ethanol, methanol, and propanol can be added.

Though the thickness of the honeycomb structure film is not particularly limited, it is preferably not more than 500 μm, and more preferably not more than 200 μm from the viewpoint of flexibility. Also, the thickness of the honeycomb structure film is preferably 1 μm or more, and more preferably 3 μm or more from the viewpoint of handling properties.

In particular, the anti-adhesion membrane of the invention is suitably used for preventing adhesion at the time of a surgical operation. For example, the adhesion preventing material is used for preventing adhesion of the surface of a biotissue as damaged by an abdominal operation against a disease of liver, spleen, pancreas, kidney, uterus, ovarium, etc. or an operation during suturing of an Achilles tendon, a nerve, etc.

With respect to a method for using the anti-adhesion membrane of the invention, an aperture of the honeycomb structure film is stuck on a wound area, and the moisture such as blood and an organ liquid is then adsorbed, thereby fixing the anti-adhesion membrane to the wound area. Since the moisture such as blood and an organ liquid is adsorbed in the aperture, it is not necessary to suture the wound area.

Furthermore, in the case where the moisture in the wound area is little so that fixation is insufficient, it is also possible to stick the anti-adhesion membrane of the invention on the wound area and then supply the liquid from the outside, thereby promoting the fixation of the subject material. As the liquid to be supplied from the outside, though any solution can be used so far as it is an aqueous solution which is harmless to the wound area, a physiological saline solution or Ringer's solution is suitable.

Moreover, since when dipped in water, the film of the invention is free from the occurrence of gelation or dissolution, it does not bond to a surgical instrument and is easy for handling.

In addition, the anti-adhesion membrane of the invention can be subjected to a sterilization treatment such as ethanol sterilization, γ-ray sterilization, electron beam sterilization, and ethylene oxide gas sterilization. By applying such a treatment, it is possible to enhance the safety.

BEST MODE FOR CARRYING OUT THE INVENTION

Modes for carrying out the invention will be hereunder described with reference to the following Examples, but it should not be construed that the invention is limited thereto.

EXAMPLES

Example 1

Figure 1:
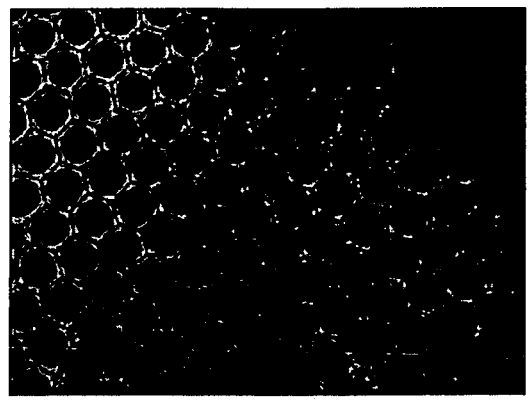
FIG. 1 is an optical microscope photograph of an anti-adhesion membrane of the invention.

A chloroform solution of polylactic acid (molecular weight: 100,000) (5 g/L) was mixed with, as an amphiphilic polymer, a polyacrylamide copolymer (weight average molecular weight: 85,000) as represented by the compound formula 1 in a proportion of 10/1, the mixture was cast on a glass substrate and allowed to stand under a condition at room temperature and at a humidity of 70%, and the solvent was gradually evaporated off to prepare a honeycomb structure. The thus obtained honeycomb structure had a size of void inner diameter of 5 μm and a film thickness of 13 μm. An optical microscope photograph thereof is shown in FIG. 1.

Example 2

A chloroform solution of a lactic acid-glycolic acid copylymer (copolymer ratio: 75/25, molecular weight: 100,000) (5 g/L) was mixed with, as an amphiphilic polymer, the polyacrylamide copolymer in a proportion of 10/1, the mixture was cast on a glass substrate and allowed to stand under a condition at room temperature and at a humidity of 70%, and the solvent was gradually evaporated off to prepare a honeycomb structure. The thus obtained honeycomb structure had a size of void inner diameter of 5 μm and a film thickness of 13 μm.

The polyacrylamide copolymer as used has the following structural formula.

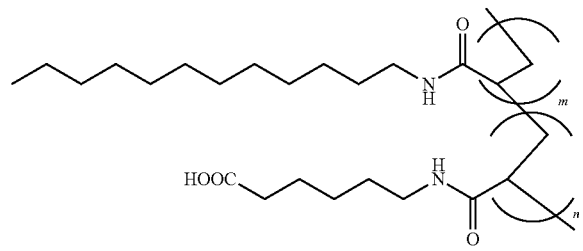

m:n = 4:1

(m and n each represents a repeating unit, and m/n is ¼.)

Comparative Example 1

A chloroform solution of polylactic acid (molecular weight: 100,000) (100 g/L) was cast on a glass substrate and allowed to stand under a condition at room temperature, and the solvent was removed by spontaneous drying to prepare a cast film.

Comparative Example 2

A chloroform solution of a lactic acid-glycolic acid copolymer (copolymer ratio: 75/25, molecular weight: 100,000) (100 g/L) was cast on a glass substrate and allowed to stand under a condition at room temperature, and the solvent was removed by spontaneous drying to prepare a cast film.

Example 3

Male SPF hairless rats (mean body weight: 250 g) were anesthetized by intraperitoneal injection; the abdominal region was cut open to expose the stomach; the integument of the wall surface of the stomach fundus was wounded about 8 mm; and each of the anti-adhesion membrane as obtained in Examples 1 and 2 and Comparative Examples 1 and 2 (three-centimeter sides) was stuck thereon every one sheet per rat. One week after sticking the anti-adhesion membrane, autopsy was performed to observe the adhesion state with the naked eye. As a result, the results regarding the adhesion state of each rat as shown in Table 1 were obtained.

In the honeycomb structure films of Examples 1 and 2, neither gelation nor dissolution was caused in the state of dipping in water, sticking to a wound area was easy because of flexibility of the film, and handling properties were good. A remarkable inflammatory response or the like was not caused, and it was noted that the anti-adhesion membrane as obtained by the invention had satisfactory biocompatibility. In each of the cast films of Comparative Examples 1 and 2, it failed in flexibility; when once wrinkled, it did not return to the original condition; and sticking to the wound area was difficult. Therefore, it could not be said that the operability is good.

The results are shown in Table 1.

TABLE 1

| | Contents of anti-adhesion membrane | Adhesion state |
|---|---|---|
| Example 1 | Honeycomb structure film made of PLA/polyacrylamide copolymer | Adhesion was not caused. |
| Example 2 | Honeycomb structure film made of PLGA/polyacrylamide copolymer | Adhesion was not caused. |
| Comparative Example 1 | PLA cast film | Adhesion was caused over peritoneum, liver and stomach. |
| Comparative Example 2 | PLGA cast film | Adhesion was caused over peritoneum, liver and stomach. |

Example 4

Figure 2:
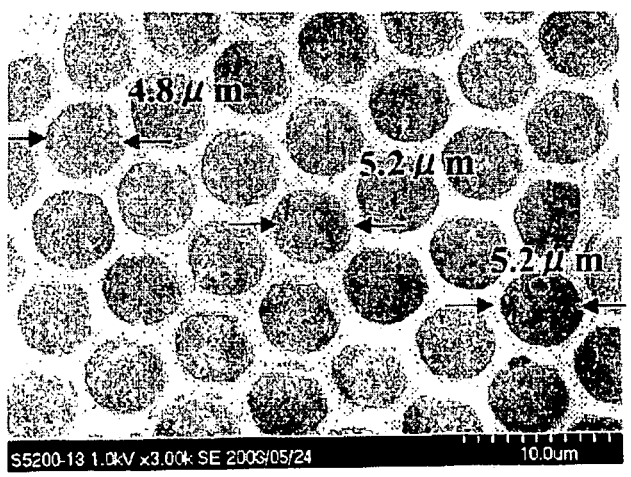
FIG. 2 is an electron microscope photograph of a film having a honeycomb structure as obtained in Example 4.

A chloroform solution of polylactic acid (molecular weight: 100,000) (5 g/L) was mixed with, as a surfactant, phosphatidyl ethanolamine-dioleoyl in a proportion of 10/1, the mixture was cast on a glass substrate and allowed to stand under a condition at room temperature and at a humidity of 70%, and the solvent was gradually evaporated off to prepare a film having a honeycomb structure. The individual pores constituting the honeycomb structure in the thus obtained structure had a size of void inner diameter of about 5 μm and a film thickness of 13 μm, and the film was a non-penetrating film. The film was cloudy. Though a polylactic acid film as prepared by a general casting method is colorless and transparent, when it has a honeycomb structure as in the invention, the film is cloudy due to scattering of light. An SEM photograph is shown in FIG. 2.

Example 5

Figure 3:
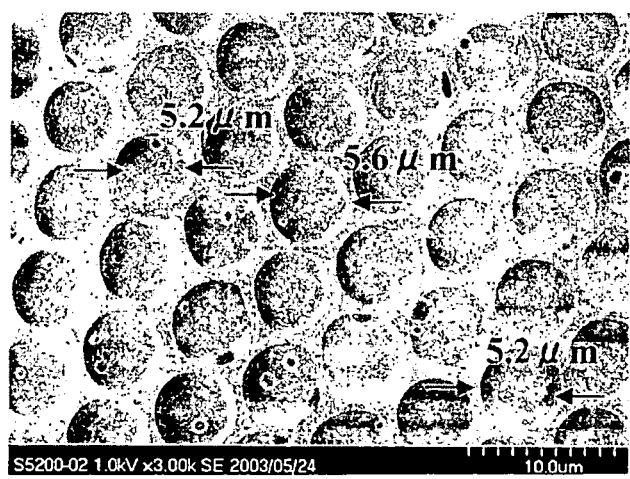
FIG. 3 is an electron microscope photograph of a film having a honeycomb structure as obtained in Example 5.

A chloroform solution of polylactic acid (molecular weight: 100,000) (5 g/L) was mixed with, as a surfactant, phosphatidyl ethanolamine-dioleoyl in a proportion of 200/1, the mixture was cast on a glass substrate and allowed to stand under a condition at room temperature and at a humidity of 70%, and the solvent was gradually evaporated off to prepare a film having a honeycomb structure. The individual pores constituting the honeycomb structure in the thus obtained structure had a size of void inner diameter of about 5 μm and a film thickness of 13 μm, and the film was a non-penetrating film. The film was cloudy. It is noted from this matter that a honeycomb structure is generated as in Example 4. An SEM photograph is shown in FIG. 3.

Example 6

Figure 4:
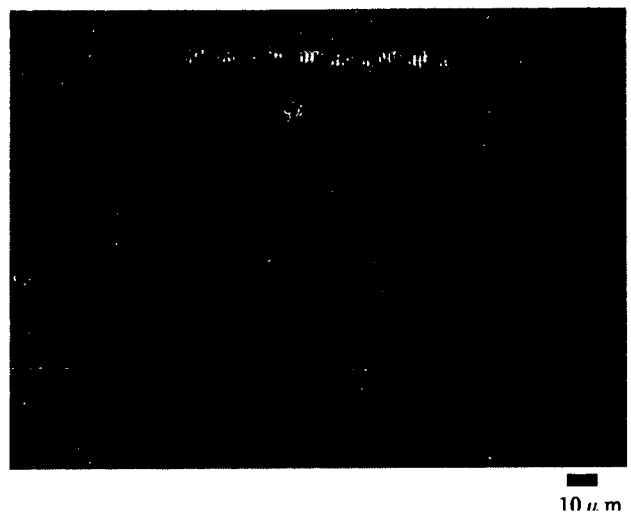
FIG. 4 is an optical microscope photograph of a film having a honeycomb structure as obtained in Example 6.

A chloroform solution of polylactic acid (molecular weight: 100,000) (5 g/L) was mixed with, as a surfactant, phosphatidyl ethanolamine-dioleoyl in a proportion of 800/1, the mixture was cast on a glass substrate and allowed to stand under a condition at room temperature and at a humidity of 70%, and the solvent was gradually evaporated off to prepare a film having a honeycomb structure. The individual pores constituting the honeycomb structure in the thus obtained structure had a size of void inner diameter of about 5 μm and a film thickness of 13 μm, and the film was a non-penetrating film. The film was cloudy. It is noted from this matter that a honeycomb structure is generated as in Example 4. An optical microscope photograph is shown in FIG. 4.

Example 7

Figure 5:
FIG. 5 is an optical microscope photograph of a film having a honeycomb structure as obtained in Example 7.

A chloroform solution of a lactic acid-glycolic acid copolymer (molecular weight: 101,000) (5 g/L) was mixed with, as a surfactant, phosphatidyl ethanolamine-dioleoyl in a proportion of 10/1, the mixture was cast on a glass substrate and allowed to stand under a condition at room temperature and at a humidity of 70%, and the solvent was gradually evaporated off to prepare a film having a honeycomb structure. The individual pores constituting the honeycomb structure in the thus obtained structure had a size of void inner diameter of about 3 μm and a film thickness of 10 μm, and the film was a non-penetrating film. The film was cloudy. Though a polylactic acid film as prepared by a general casting method is colorless and transparent, when it has a honeycomb structure as in the invention, the film is cloudy due to scattering of light. An optical microscope photograph is shown in FIG. 5.

Example 8

Figure 6:
FIG. 6 is an optical microscope photograph of a film having a honeycomb structure as obtained in Example 8.

A chloroform solution of a lactic acid-glycolic acid copolymer (molecular weight: 101,000) (5 g/L) was mixed with, as a surfactant, phosphatidyl ethanolamine-dioleoyl in a proportion of 200/1, the mixture was cast on a glass substrate and allowed to stand under a condition at room temperature and at a humidity of 70%, and the solvent was gradually evaporated off to prepare a film having a honeycomb structure. The individual pores constituting the honeycomb structure in the thus obtained structure had a size of void inner diameter of about 5 μm and a film thickness of 10 μm, and the film was a non-penetrating film. The film was cloudy. It is noted from this matter that a honeycomb structure is generated as in Example 7. An optical microscope photograph is shown in FIG. 6.

Comparative Example 3

It was tried to prepare a film having a honeycomb structure in the same manner as in Example 4 by using a chloroform solution of polylactic acid (molecular weight: 100,000) (5 g/L). However, a honeycomb structure was not formed, but a non-uniform film was prepared.

Comparative Example 4

It was tried to prepare a honeycomb structure in the same manner as in Example 1 by using a chloroform solution of phosphatidyl ethanolamine-dioleoyl (5 g/L). However, a film could not be prepared, and self-supporting properties were not revealed.

In order to confirm the adhesion preventive effect in a living body according to the invention of this application, experiments were carried out by using an intraperitoneal adhesion model of rat.

With respect to the intraperitoneal adhesion model, a rat was fixed in the supination under the anesthesia by intraperitoneal administration with sodium pentobarbital (30 mg/kg Nembutal injection, available from Dainippon Pharmaceutical Co., Ltd.), and the abdominal region was shaven and then disinfected with ethanol for disinfection. In addition, the operation region was disinfected with an isodine disinfectant, and from 3 to 4 cm of the abdominal region was then cut open along the median line to expose a cecum. A certain area (1 to 2 cm$^2$) of the exposed caecum was abraded by using a sterile absorbent gauze until petechial hemorrhage was generated. After returning the caecum into the peritoneal cavity, the anti-adhesion membrane was stuck thereon, the tunica muscularis of the cut part was continuously sutured, and the cutis was sutured with 4 to 5 stitches. The wound part was disinfected with an isodine disinfectant, and the rat was then returned to a cage.

Seven days after the operation, the rat was subjected to an operation on the abdomen under the anesthesia with sodium pentobarbital, and the degree of intraperitoneal adhesion was observed with the naked eye and scored according to the following criteria.

(Grade Classification)

Grade 0 (score 0): Adhesion is not found.

Grade 1 (score 1): Adhesion is found to a degree such that the adhesion is fine and can be easily separated out.

Grade 2 (score 2): Weak adhesion is found to a degree such that the adhesion is generated within a narrow range but is durable against a slight degree of the traction.

Grade 3 (score 3): Considerably firm adhesion is found or adhesion is found in at least two places.

Grade 4 (score 4): Adhesion is found in three or more places.

Example and Comparative Examples will be described below.

Example 9

An adhesion preventive effect in a living body was confirmed by using the film as obtained in Example 5.

Comparative Example 5

The rat was sutured according to the same procedures as in the foregoing intraperitoneal adhesion model without using an anti-adhesion membrane.

Comparative Example 6

An intraperitoneal adhesion model was carried out by using Sepra film(™) (sodium hyaluronate and carboxymethyl cellulose, thickness: about 55 μm, available from Kaken Pharmaceutical Co., Ltd.).

The degree of intraperitoneal adhesion on each animal was scored according to the grade classification, and the results as expressed in terms of {(mean value)±(standard error)} (mean±S.E.) are shown in Table 2.

A mean adhesion score of Comparative Example 5 (without a film) was 3.0±0.3. On the other hand, a mean adhesion score of Example 7 was 1.6±0.5, and a reduction of the adhesion score was observed as compared with Comparative Example 5. Similarly, a reduction of the adhesion score was also observed as compared with the adhesion score (1.8±0.7) of Comparative Example 6 (with Ceprafilm).

The anti-adhesion membrane of the invention of this application gives rise to an explicit effect as compared with the case where an anti-adhesion membrane is not used. Furthermore, not only it is effective for preventing adhesion as compared with the film of Comparative Example 6 which is currently put into practical use, but also it is easy in handling because it does not have bonding properties as in the film of Comparative Example 6.

TABLE 2

Results of evaluation of intraperitoneal adhesion model

| Drug | Animal No. | Score |
| --- | --- | --- |
| Example 9: | | |
| Honeycomb film | 301 | 0 |
| PLA/PE = 200/1 | 302 | 2 |
| | 303 | 1 |
| | 304 | 3 |
| | 305 | 2 |
| | Mean | 1.6 |
| | ±S.E. | 0.5 |
| Comparative Example 5: | | |
| Control group | 101 | 4 |
| (without a film) | 102 | 2 |
| | 103 | 3 |
| | 104 | 3 |
| | 105 | 3 |
| | Mean | 3.0 |
| | ±S.E. | 0.3 |
| Comparative Example 6: | | |
| Positive control group | 201 | 1 |
| (with Ceprafilm) | 202 | 4 |
| | 203 | 1 |
| | 204 | 3 |
| | 205 | 0 |
| | Mean | 1.8 |
| | ±S.E. | 0.7 |

INDUSTRIAL APPLICABILITY

The biodegradable film having a honeycomb structure of the invention of this application can be applied as an anti-adhesion membrane to a living body.

The invention claimed is:

1. A biodegradable film having a honeycomb structure and comprising a biodegradable polymer and a surfactant, which is characterized in that said surfactant is a dioleoylphosphatidylethanolamine.

2. The biodegradable film having a honeycomb structure according to claim 1, wherein said biodegradable polymer is a biodegradable aliphatic polyester and/or a biodegradable aliphatic polycarbonate.

3. The biodegradable film having a honeycomb structure according to claim 2, wherein said biodegradable aliphatic polyester is at least one polymer selected from the group consisting of polylactic acid, a polylactic acid-polyglycolic acid copolymer, polyhydroxybutyric acid, polycaprolactone, polyethylene adipate, and polybutylene adipate.

4. The biodegradable film having a honeycomb structure according to claim 2, wherein said biodegradable aliphatic polycarbonate is at least one polymer selected from the group consisting of polybutylene carbonate and polyethylene carbonate.

5. The biodegradable film having a honeycomb structure according to any one of claims 1 to 3, which is characterized in that said biodegradable polymer is polylactic acid or a lactic acid-glycolic acid copolymer.

6. The biodegradable film having a honeycomb structure according to claim 1, which is characterized in that said dioleoylphosphatidylethanolamine is L-α-phosphatidyl ethanolamine dioleoyl.

7. The biodegradable film having a honeycomb structure according to claim 1, which is characterized in that a composition ratio of said biodegradable polymer to said dioleoylphosphatidylethanolamine is from 1/1 to 1,000/1.

8. An anti-adhesion membrane comprising the biodegradable film according to claim 1 or 2.

9. The anti-adhesion membrane according to claim 8, which is characterized in that the honeycomb structure has a mean void inner diameter of not more than 20 μm.

10. The anti-adhesion membrane according to claim 9, which is characterized in that only one surface of the film has the honeycomb structure.

11. A process for producing a biodegradable film according to claim 1, comprising casting a mixture of an organic solvent solution of a biodegradable polymer and dioleoylphosphatidylethanolamine on a substrate in a humid atmosphere having a relative humidity of from 50 to 95%, gradually evaporating said organic solvent and simultaneously condensing it on the surface of said cast liquid, and evaporating fine water droplets as generated by said condensation.

12. The production process of a biodegradable film according to claim 11, wherein said biodegradable polymer is a biodegradable aliphatic polyester.

* * * * *